US011783918B2

(12) United States Patent
Strauss et al.

(10) Patent No.: US 11,783,918 B2
(45) Date of Patent: Oct. 10, 2023

(54) DNA RANDOM ACCESS STORAGE SYSTEM VIA LIGATION

(71) Applicant: Microsoft Technology Licensing, LLC, Redmond, WA (US)

(72) Inventors: Karin Strauss, Seattle, WA (US); Yuan-Jyue Chen, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 865 days.

(21) Appl. No.: 16/464,111

(22) PCT Filed: Oct. 30, 2017

(86) PCT No.: PCT/US2017/058997
§ 371 (c)(1),
(2) Date: May 24, 2019

(87) PCT Pub. No.: WO2018/102064
PCT Pub. Date: Jun. 7, 2018

(65) Prior Publication Data
US 2019/0376120 A1 Dec. 12, 2019

Related U.S. Application Data

(60) Provisional application No. 62/428,431, filed on Nov. 30, 2016.

(51) Int. Cl.
*C12Q 1/6806* (2018.01)
*C12Q 1/6869* (2018.01)
*G16B 50/30* (2019.01)
*G16B 50/00* (2019.01)

(52) U.S. Cl.
CPC .......... *G16B 50/30* (2019.02); *C12Q 1/6806* (2013.01); *C12Q 1/6869* (2013.01); *G16B 50/00* (2019.02)

(58) Field of Classification Search
None
See application file for complete search history.

(56) References Cited

U.S. PATENT DOCUMENTS

| | | | |
|---|---|---|---|
| 6,828,098 | B2 | 12/2004 | Langmore et al. |
| 7,194,504 | B2 | 3/2007 | Moulton |
| 8,769,689 | B2 | 7/2014 | Hoglund |
| 8,806,127 | B2 | 8/2014 | Brownell et al. |
| 9,098,523 | B2 | 8/2015 | Bhola et al. |
| 9,384,320 | B2 | 7/2016 | Church |
| 10,030,261 | B2 | 7/2018 | Frisen et al. |
| 2004/0209299 | A1 | 10/2004 | Pinter et al. |
| 2005/0053968 | A1 | 3/2005 | Bharadwaj et al. |
| 2008/0131886 | A1 | 6/2008 | Ji et al. |
| 2011/0217738 | A1 | 9/2011 | Jacobson |
| 2014/0236490 | A1 | 8/2014 | Van rooyen et al. |
| 2014/0274729 | A1 | 9/2014 | Kurn et al. |
| 2015/0133319 | A1* | 5/2015 | Fu ...................... C12N 15/1065 506/4 |
| 2015/0261664 | A1 | 9/2015 | Goldman et al. |
| 2018/0223340 | A1 | 8/2018 | Chen et al. |
| 2018/0223341 | A1 | 8/2018 | Chen et al. |

FOREIGN PATENT DOCUMENTS

| | | |
|---|---|---|
| CA | 2940764 A1 | 9/2015 |
| CN | 1230226 A | 9/1999 |
| CN | 103805713 A | 5/2014 |
| CN | 104619894 A | 5/2015 |
| CN | 104919056 A | 9/2015 |
| CN | 105264092 A | 1/2016 |
| CN | 106029891 A | 10/2016 |
| EP | 1136932 A1 | 9/2001 |
| WO | 2008015396 A2 | 2/2008 |
| WO | 2008023179 A2 | 2/2008 |
| WO | 2008096146 A1 | 8/2008 |
| WO | 2012103154 A1 | 8/2012 |

(Continued)

OTHER PUBLICATIONS

Raine, Splinted Ligation Adapter Tagging (SPLAT), a novel library preparation method for whole genome bisulphite sequencing, Nucleic Acids Research, 45(6): 1-15, published online Nov. 29, 2016. (Year: 2016).*
"Notice of Allowance Issued in European Patent Application No. 18705779.9", dated Mar. 22, 2022, 7 Pages.
"Office Action Issued in Indian Patent Application No. 201947022685", dated Mar. 31, 2022, 6 Pages.
"Office Action Issued in Indian Patent Application No. 201947031220", dated Jan. 24, 2022, 6 Pages.
"An Introduction to Next-Generation Sequencing Technology", Retrieved From: https://web.archive.org/web/20170303034320/https://www.ramaciotti.unsw.edu.au/wp-content/uploads/2015/09/illumina_sequencing_introduction.pdf, Mar. 3, 2017, 16 Pages.
"PCR Primer Design Guidelines", Retrieved From: https://web.archive.org/web/20161221065135/http://www.premierbiosoft.com/tech_notes/PCR_Primer_Design.html, Dec. 21, 2016, 4 Pages.

(Continued)

*Primary Examiner* — Angela M. Bertagna
*Assistant Examiner* — Carolyn L Greene
(74) *Attorney, Agent, or Firm* — Benjamin Keim; Newport IP, LLC

(57) ABSTRACT

Techniques for random access of particular DNA strands from a mixture of DNA strands are described. DNA strands that encode pieces of the same digital file are labeled with the same identification sequence. The identification sequence is used to selectively separate DNA strands that contain portions of the same digital file from other DNA strands. A DNA staple positions DNA strands with the identification sequence adjacent to sequencing adaptors. DNA ligase joins the molecules to create a longer molecule with the region encoding the digital file flanked by sequencing adaptors. DNA strands that include sequencing adaptors are sequenced and the sequence data is available for further analysis. DNA strands without the identification sequence are not joined to sequencing adaptors, and thus, are not sequenced. As a result, the sequencing data produced by the DNA sequencer comes from those DNA strands that included the identification sequence.

20 Claims, 6 Drawing Sheets

(56) References Cited

FOREIGN PATENT DOCUMENTS

| WO | 2013134341 A1 | 9/2013 |
| WO | 2013178801 A2 | 12/2013 |
| WO | 2013184754 A2 | 12/2013 |
| WO | 2014196863 A1 | 12/2014 |
| WO | 2015121236 A1 | 8/2015 |
| WO | 2015144858 A1 | 10/2015 |
| WO | 2016164779 A1 | 10/2016 |
| WO | 2016168351 A1 | 10/2016 |

OTHER PUBLICATIONS

"Primer3Plus", Retrieved From: https://web.archive.org/web/20081202150612/http://www.bioinformatics.nl/cgi-bin/primer3plus/primer3plus.cgi, Dec. 2, 2008, 1 Page.

Blawat, et al., "Forward Error Correction for DNA Data Storage", In Proceedings of the International Conference on Computational Science, Jan. 1, 2016, pp. 1011-1022.

Blawat, et al., "Storing movies in DNA", Retrieved From: https://www.afcinema.com/IMG/pdf/technicolor_storing_movies_in_dna.pdf. Retrieved Date: Aug. 17, 2016, pp. 38-42.

Bornholt, et al., "A DNA-Based Archival Storage System", In Proceedings of 21th ACM International Conference an Architectural Support for Programming Languages and Operating Systems, Apr. 2, 2016, pp. 637-649.

Church, et al., "Next-Generation Digital Information Storage in DNA", In Journal of Science, vol. 337, Aug. 16, 2012, pp. 1-2.

De Simone, Sergio, "Microsoft Experimenting with Using Synthetic DNA for Digital Data Storage", https://www.infoq.com/news/2016/05/microsoft-dna-storage, May 1, 2016, pp. 5-11.

Georgescu, et al., "Mechanism of Polymerase Collision Release from Sliding Clamps on the Lagging Strand", In Journal of European Molecular Biology Organization, vol. 28, Issue 19, Aug. 20, 2009, pp. 2981-2991.

Goela, et al., "Encoding Movies and Data in DNA Storage", In Proceedings of Information Theory and Applications Workshop (ITA), Jan. 31, 2016, 1 Page.

Goldman, et al., "Towards Practical, High-Capacity, Low-Maintenance Information Storage in Synthesized DNA", In Journal of Nature, vol. 494, Feb. 7, 2013, pp. 77-80.

Horton, Robert M., "PCR Primer Design", Retrieved From: https://web.archive.org/web/20130419060311/http://www.cybertory.org/exercises/primerDesign/, Apr. 19, 2013, 8 Pages.

Laddha, et al., "Digital Data Storage on DNA", In International Journal of Computer Applications, vol. 142, No. 02, May 2016, pp. 43-46.

Limbachiya, et al., "Natural Data Storage: A Review on Sending Information From Now to then via Nature", In Journal of the Computing Research Repository, May 19, 2015, 17 Pages.

Martin, Luther, "Collisions in a Hash Function from DNA Testing", Retrieved From: https://web.archive.org/web/20160410084033/https://www.voltage.com/security/collisions-in-a-hash-function-from-dna-testing/, Jun. 19, 2012, 1 Page.

Mearian, Lucas, "Microsoft, University Researchers break DNA data Storage Record", Retrieved From: https://web.archive.org/web/20160710043750/https://www.computerworld.com/article/3093467/data-storage/dna-data-storage-record-broken-by-microsoft-university-researchers.html, Jul. 8, 2016, 6 Pages.

"International Search Report and Written Opinion Issued in PCT Application No. PCT/US2017/058997", dated Feb. 26, 2018, 10 Pages.

"International Search Report and Written Opinion Issued in PCT Application No. PCT/US2018/016327", dated May 7, 2018, 13 Pages.

"International Search Report and Written Opinion Issued in PCT Application No. PCT/US2018/016530", dated Jun. 4, 2018, 16 Pages.

Fan, Shelly, "This Droplet of DNA Could Store 600 Smartphones Worth of Retrievable Data", Retrieved from: https://singularityhub.com/2016/04/17/this-droplet-of-dna-could-store-600-smartphones-worth-of-retrievable-data/#sm.0001mi841fyxddoqr322hqlvbrv4j, Apr. 17, 2016, 4 Pages.

Simmler, et al., "Real-Time Primer Design for DNA Chips", In Proceedings of Second IEEE International Workshop an High Performance Computational Biology, Apr. 22, 2003, 8 Pages.

Yazdi, et al., "A Rewritable, Random-Access DNA-Based Storage System", In Journal of Scientific Reports, vol. 5, Sep. 18, 2015, 26 Pages.

Ye, et al., "Primer-BLAST: A Tool to Design Target-Specific Primers for Polymerase Chain Reaction", In Journal of BMC Bioinformatics, vol. 13, Issue 1, Dec. 1, 2012, 11 Pages.

"Office Action Issued in European Patent Application No. 18705779.9", dated Dec. 22, 2020, 13 Pages.

"Non Final Office Action Issued in U.S. Appl. No. 15/427,344", dated Feb. 6, 2020, 10 Pages.

"First Office Action and Search Report Issued in Chinese Patent Application No. 201880010803.1", dated Sep. 5, 2022, 13 Pages.

Das, et al., "A Highly Secure DNA Based Image Steganography", In Proceedings of the International Conference on Green Computing Communication and Electrical Engineering, Mar. 6, 2014, 5 Pages.

"Attenuation of Goose Paramyxovirus Strain NA-1 by Reverse Genetics", In Dissertation Submitted to JLIN University, Sep. 30, 2011, 78 Pages.

"Decision to Grant Issued in European Patent Application No. 18705779.9", Mailed Date: Jun. 30, 2022, 2 Pages.

"First Office Action and Search Report Issued in Chinese Patent Application No. 201780073909.1", dated Dec. 5, 2022, 12 Pages.

"Notice of Allowance Issued in Chinese Patent Application No. 201780073909.1", dated Apr. 27, 2023, 8 Pages.

* cited by examiner

DNA RANDOM ACCESS STORAGE SYSTEM VIA LIGATION

PRIORITY APPLICATION

This application is a National Phase and claims priority to PCT Application Serial Number PCT/US2017/58997, entitled "DNA RANDOM ACCESS STORAGE SYSTEM VIA LIGATION," filed Oct. 30, 2017, which claims priority to U.S. Provisional Application Ser. No. 62/428,431 (entitled DNA Random Access Storage System via Ligation, filed Nov. 30, 2016) which are incorporated herein by reference.

BACKGROUND

Polymers of deoxyribose nucleic acid (DNA) are capable of storing information at high density. A gram of DNA contains about $10^{21}$ DNA nucleotides (nt) which can encode about $10^8$ terabytes of data. The information density of DNA is about $10^8$ times more compact than other types of storage media. Less than 100 grams of DNA could store all the human-made data in the world. Thus, DNA is appealing as an information storage technology because of its high information density. Information encoded by DNA is first converted to a format that can be processed by digital computing technology before presentation in a human-readable form. Converting everything in a DNA of digital data storage pool into electronic format whenever any information from that pool is desired would be inefficient and negate much of the advantage of storing the information as DNA. Techniques to identify particular DNA strands containing information of interest reduce the amount of information that is converted into electronic format and can improve the usability of DNA as an information storage medium.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

Selectively pulling only desired DNA strands out of storage requires some way of differentiating one DNA strand from another. The techniques described herein use an identification (ID) sequence that is included on DNA strands which share some commonality such as, for example, all encoding a portion of the same digital file. A given pool of DNA may include thousands or millions of DNA strands with different ID sequences. A relatively short DNA strand referred to herein as a "staple" includes one portion that hybridizes to a particular ID sequence and another portion that hybridizes to part of a sequencing adaptor. A sequencing adaptor is another DNA strand that is used to adapt a DNA strand of interest so that it can be read by a DNA sequencer.

Due to the staple hybridizing to part of DNA strands that include the particular ID sequence and hybridizing to part of the sequencing adaptor, the staple serves to bring DNA strands with the particular ID sequence adjacent to the sequencing adaptor. DNA ligase forms a covalent bond between the DNA strands and the sequencing adaptors. This creates new, longer DNA strands that include a payload, that may represent a portion of a digital file, and sequencing adaptors. Due to the specificity of the staple and the difference in ID sequences other DNA strands that do not include the same ID sequence will not be joined to a sequencing adaptor. At this point, the various DNA strands may still be undifferentiated and mixed together in the DNA store. However, only those DNA strands with the known ID sequence are joined to sequencing adaptors. Thus, when the entire contents of the DNA store are sequenced, molecules without the sequence adaptors will be ignored by the DNA sequencer and the output of the DNA sequencer will include only the sequences of those DNA strands that have the particular ID sequence.

This provides arbitrary and random access to any group of DNA strands that share the same ID sequence from within a pool of multiple different DNA strands.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
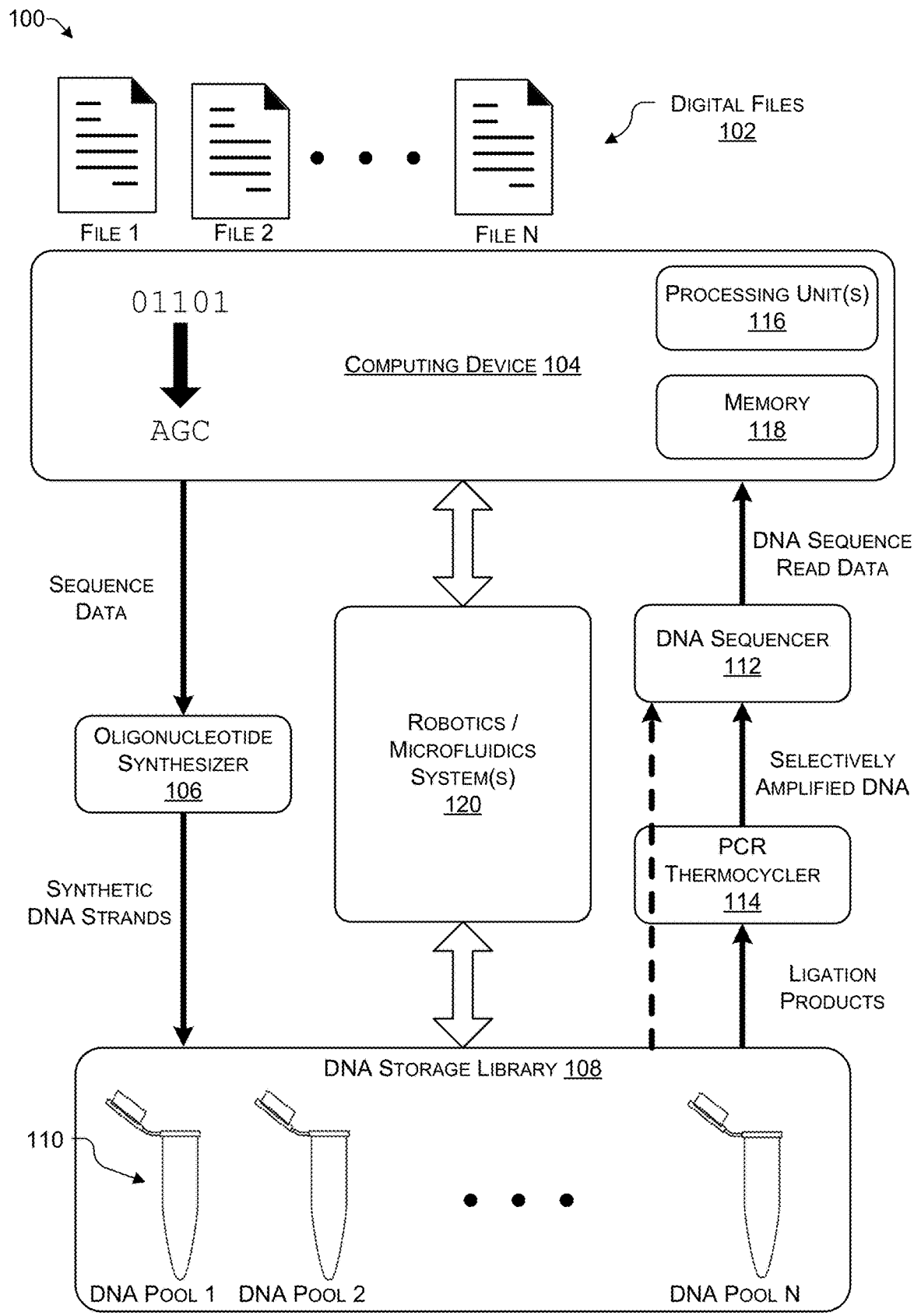
FIG. 1 shows an illustrative schematic of a system for providing arbitrary, random-access to DNA strands stored in a DNA pool.

If digital information is stored in DNA, the ability to randomly access specific pieces of that information without having to first convert all of the DNA-encoded-information into digital data provides greater efficiencies in terms of DNA sequencer bandwidth and provides the type of access that is currently expected from information storage systems. Specifically, "random access" refers to the ability to access data at any arbitrary portion of the memory specified by a user. The opposite of random access is sequential access. To go from point A to point Z in a sequential-access system, the system must access all intervening points. In a random-access system, the system can jump directly to point Z. Disks are random access media, whereas tapes are sequential access media. A DNA sequencer reading a single DNA strand is sequential access. However, when digital information is stored in a large number of DNA strands, selectively pulling out and sequencing only those DNA strands that contain the desired information is random access.

One technique for providing random access to DNA strands storing digital information is to identify DNA strands by ID sequences that are primer sites for polymerase chain reaction (PCR) amplification. DNA strands storing related digital information (e.g. portions of the same digital file stored as DNA) may share the same primer sites, so amplification with a given pair of primers selectively increases the numbers of those DNA strands while DNA strands with different primer sites do not increase. A DNA sequencer will detect the more numerous DNA strands and generate a sequence output that includes the selected information. Some challenges with a primer-based random access include formation of secondary structures by the primers, nonspecific annealing which can lead to amplification of incorrect DNA strands, and amplification bias due to differences in primer efficiency. The ligation-based approach for achieving random access described in this disclosure is different and addresses the challenges with primer-based random access.

The term "primer" as used herein refers to an oligonucleotide which is capable of acting as a point of initiation of nucleic acid synthesis when placed under conditions in which synthesis of a primer product, which is complementary to a nucleic acid strand, is induced, i.e., in the presence of four different nucleotide triphosphates with appropriate enzymes at a suitable temperature and salt concentration. Specific length and sequence will depend on the complexity of the required primer targets, as well as on the conditions of primer use such as temperature and ionic strength. In some implementations, a primer can be 5-50 nt, 10-25 nt, or 15-20 nt in length. The fact that amplification primers do not have to match exactly with the corresponding template sequence to warrant proper amplification is amply documented in the literature. It is generally accepted that a typical length of PCR primers is 18-22 nt. This length is long enough for adequate specificity and short enough for primers to bind easily to the template at the annealing temperature.

Naturally occurring DNA strands consist of four types of nucleotides: adenine (A), cytosine (C), guanine (G), and thymine (T). A DNA strand, or polynucleotide, is a linear sequence of these nucleotides. The two ends of a DNA strand, referred to as the 5' and 3' ends, are chemically different. DNA sequences are conventionally represented starting with the 5' nucleotide end at the left. The interactions between different strands are predictable based on sequence: two single strands can bind to each other and form a double helix if they are complementary: A in one strand aligns with T in the other, and likewise for C and G. The two strands in a double helix have opposite directionality (5' end attached to the other strand's 3' end), and thus the two sequences are the "reverse complement" of each other. Two strands do not need to be fully complementary to bind to one another. Ribonucleic acid (RNA) has a similar structure to DNA and naturally occurring RNA consists of the four nucleotides A, C, G, and uracil (U) instead of T. Discussions in this disclosure mention only DNA for the sake of brevity and readability, but RNA may be used in place of or in combination with DNA. RNA may also bind to DNA forming a hybrid molecule.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

"Hybridizing" as used herein means placing two complementary single-strand (ss) DNA strands in conditions that allow hybridization to form a double-strand (ds) DNA strand or causing two complementary ssDNA strands to hybridize and form a dsDNA strand. Hybridization may be performed under high stringency conditions.

Artificial synthesis of DNA allows for creation of DNA strands with arbitrary series of the nucleotides. The order in which individual monomers of these four nucleotides are assembled together into a polymer can represent information in an analogous manner as 0 and 1 in digital computers. Thus, multiple DNA strands can be synthesized with particular orders of the four DNA nucleotides and encode large amounts of information. The information is encoded as a series of DNA nucleotides, but may represent any type of data such as text, audio files, video files, or anything else that may be encoded by conventional binary data recording in electronic computers. Various techniques for converting information from digital files into DNA are discussed elsewhere such as in U.S. patent application Ser. No. 15/004, 827.

FIG. 1 shows a system 100 that can convert digital files 102 into DNA strands that encode equivalent information as the digital files. A digital or computer file is a stored segment or block of information that is available to a computer program. A computing device 104 can convert the 0's and 1's of binary information into a string of letters that represent nucleotides found in DNA. The computing device 104 generates sequence data which is a series of letters corresponding to DNA nucleotides that represent the data from a digital file 102. At this stage, the sequence data is still electronic data representing a series of letters. In addition to sequence data that represents a portion of a digital file 102, the sequence data may also include staple sequences, primer sequences, and sequencing adaptor sequences.

An oligonucleotide synthesizer 106 converts sequence data received from the computing device 104 into synthetic DNA strands. A number of methods for DNA synthesis and commercial oligonucleotide synthesizers are available and known to those skilled in the art. Methods for DNA synthesis include solid-phase phosphoramidite synthesis, microchip-based oligonucleotide synthesis, ligation-mediated assembly, PCR-mediated assembly, and the like. Examples of oligonucleotide synthesizers 106 include ABI 394 DNA Synthesizer (Applied Biosystems, Foster City, Calif.), the Piezoelectric Oligonucleotide Synthesizer And Microarrayer (POSAM), photolithographic oligoarray synthesizers, etc.

The synthetic DNA strands are placed into a DNA storage library 108. The DNA storage library 108 may be divided into one or more DNA pools 110. Each DNA pool 110 represents a physical location within which there are no further physical or structural subdivisions between DNA strands. Separating the content of different files 102 into different DNA pools 110 is one technique for providing random access to individual files. In this example, random access is provided by physical positions of numerous DNA pools 110. However, due to the high information density of DNA it is possible to store the information from many different digital files 102 in a very small volume. Accordingly, not mixing DNA from different digital files 102 would greatly limit the density with which information could be stored in DNA.

Given a DNA pool 110 that contains a large number of DNA strands representing data from several different digital files 102, retrieving data that corresponds to one or several selected digital files 102 requires a technique that uses the DNA strands themselves to determine which digital file 102 a given DNA strand corresponds to.

Each of the DNA strands may be present in the DNA pool 110 as a single-stranded molecule or may hybridize to a complementary ssDNA strand to form double stranded DNA. dsDNA may be converted to ssDNA if desired by using asymmetric PCR or another technique. Asymmetric PCR uses an unequal amount of the two primers. A large excess of one of the primers is added to the reaction creating an excess of ssDNA. Creation of ssDNA from dsDNA is well known to those of ordinary skill in the art. See Gyllensten, U. B., and H. A. Erlich. *Generation of single-stranded DNA by the polymerase chain reaction and its application to direct sequencing of the HLA-DQA locus.* 85 Proc. Natl. Acad. Sci. USA 7652-7656 (1988); McCabe, P. C. *Production of single-stranded DNA by asymmetric PCR.* In M. A. Innis, D. H. Gelfand, and J. J. Sninsky (Eds.) *PCR Protocols, A Guide to Methods and Applications.* Academic Press, New York: 76 (1990); and X. S., D. Y. Zhang, and G. Seelig, *Conditionally fluorescent molecular probes for detecting single base changes in double-stranded DNA,* 5 Nature Chemistry 782 (2013).

The DNA strands may be stored in solution or another format such as lyophilized, in silica glass spheres, etc. DNA corresponding to a particular digital file 102 is retrieved from a DNA pool 110 based on ID sequences included in the DNA strand. Correspondence between the ID sequences and a particular digital file 102 may be stored in the memory 118 of the computing device 104 such as, for example in a lookup table. Prior techniques have used PCR primer sites as the ID sequences. Addition of the appropriate primers and amplification with PCR greatly increases the number of copies of those DNA strands that include the primer sites. DNA sequencing reads the amplified copies, and due to the vast difference in numbers, the un-amplified copies are not represented in the sequencing output. As will be discussed in greater detail below, the techniques of this disclosure use ID sequences on the DNA strands in a different way. Instead of introducing primers to a DNA pool 110, the oligonucleotide synthesizer 106 may be used to introduce short pieces of DNA called "staples" that hold DNA strands with the ID sequences adjacent to sequencing adaptors that facilitate DNA sequencing. The enzyme DNA ligase is used to connect the DNA strands with the sequencing adaptors into a single, longer DNA strand that includes the DNA sequence representing a portion of the digital file 102 flanked by sequencing adaptors. This is called a ligation product because it is produced as a result of ligating multiple DNA strands together.

The ligation products exist in the DNA pool 110 or another vessel or container into which the DNA strands from the DNA pool 110 may be transferred. For example, the vessel or container, may be an Eppendorf tube, a thermal cycler/PCR tube, a microfluidics chamber, etc. The ligation products are DNA strands that include sequencing adaptors for use by DNA sequencer 112. Sequencing adaptors are well known to those skilled in the art. Different sequencing techniques and machines use different adaptors. Head, Steven R. et al. "*Library Construction for next-Generation Sequencing: Overviews and Challenges.*" BioTechniques 56.2 (2014): 61—passim.

Once sequencing adaptors are attached to the DNA strands of interest through ligation, the ligation products may be provided directly to a DNA sequencer 112 for sequencing as shown by the dashed line from the DNA storage library 108 to the DNA sequencer 112. Other DNA strands in the DNA pool 110 will not have sequencing adaptors because those DNA strands did not have the ID sequence which allowed for hybridization of the staples. The DNA sequencer 112 may use any technique for sequencing that makes use of sequencing adaptors. For example, the DNA sequencer 112 may use sequencing-by-synthesis, parallel pyrosequencing, single molecule real time sequencing (SMRT), SOLiD (Sequencing by Oligonucleotide Ligation and Detection), or other sequencing technology known to those skilled in the art.

Alternatively, the DNA strands may be amplified prior to sequencing in the DNA sequencer 112. Any of several methods can be used to amplify a target nucleic acid from a sample. The term "amplifying" which typically refers to an "exponential" increase in the number of copies of the target nucleic acid is used herein to describe both linear and exponential increases in the numbers of a select target sequence of nucleic acid. The term "amplification reaction mixture" refers to an aqueous solution comprising the various reagents used to amplify a target nucleic acid. These include enzymes, including, polymerases, and thermostable polymerases such as DNA polymerase, RNA polymerase and reverse transcriptase, aqueous buffers, salts, amplification primers, target nucleic acid, and nucleoside triphosphates. Depending upon the context, the mixture can be either a complete or incomplete amplification reaction mixture. The method used to amplify the target nucleic acid can be any method available to one of skill in the art.

One technique for amplification is PCR which may use a PCR thermocycler 114. A variety of PCR techniques are known and can be used with the techniques described herein. PCR techniques are typically used for the amplification of at least a portion of an oligonucleotide. The sample to be tested for the presence of an analyte-specific sequence is contacted with the first and second oligonucleotide primers; a nucleic acid polymerase; and nucleotide triphosphates corresponding to the nucleotides to be added during PCR. The natural base nucleotide triphosphates include dATP, dCTP, dGTP, dTTP, and dUTP. Nucleoside triphosphates of non-standard bases can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I and the HIV-1 polymerase.

The entire contents of the DNA pool 110, or other vessel containing the DNA to be analyzed, may be placed in the PCR thermocycler 114. The process of PCR is well known to those skilled in the art and has been extensively characterized. PCR involves the following three steps: denaturation, annealing, and extension. First, any dsDNA is denatured, converting to single strands. The primers are then annealed to the complementary regions of the single stranded molecules. In the third step, the primers are extended by the action of the DNA polymerase. All these steps are temperature sensitive and a common choice of temperatures is 94° C., 60° C., and 70° C., respectively. In order to amplify the sequencing adaptors together with the DNA encoding a portion of the digital file 102, the primers are designed to hybridize with the ends of the sequencing adaptors in order to create multiple copies of the ligation products. Melting Temperature ($T_m$) by definition is the temperature at which one half of a DNA duplex will dissociate to become single stranded and indicates the duplex stability. Primers with melting temperatures in the range of 52-58° C. generally produce the best results. Primers with melting temperatures above 65° C. have a tendency for secondary annealing. The GC content of the sequence gives a fair indication of the primer $T_m$. Other DNA strands from the DNA pool 110 will still be present during PCR, but primers present in the PCR mix will be unlikely to hybridize with those DNA strands. The selectively amplified DNA generated by the PCR thermocycler 114 may be provided to the DNA sequencer 112. PCR amplification prior to sequencing improves the yield and may convert ssDNA to dsDNA which improves the stability and longevity of DNA in storage.

The output from the DNA sequencer 112 is electronic data including a series of letters that represent the nucleotides in the DNA strands provided to the DNA sequencer 112. This electronic data is returned to the computing device 104, or to a different computing device, converted to binary data, further analyzed, errors are corrected, and ultimately reassembled into a digital file 102.

The computing device 104 may include one or more processing units 116 and memory 118, both of which may be distributed across one or more physical or logical locations. The processing unit(s) 116 may include any combination of central processing units (CPUs), graphical processing units (GPUs), single core processors, multi-core processors, processor clusters, application-specific integrated circuits (ASICs), programmable circuits such as Field Programmable Gate Arrays (FPGA), and the like. One or more of the processing unit(s) 116 may be implemented in software or firmware in addition to hardware implementations. Software or firmware implementations of the processing unit(s) 116 may include computer- or machine-executable instructions written in any suitable programming language to perform the various functions described. Software implementations of the processing unit(s) 116 may be stored in whole or part in the memory 118.

Alternatively or additionally, the functionality of computing device 104 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Memory 118 of the computing device 104 may include removable storage, non-removable storage, local storage, or remote storage to provide storage of computer-readable instructions, data structures, program modules, and other data. The memory 118 may be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer-readable instructions, data structures, program modules, or other data in a modulated data signal, such as a carrier wave, or other transmission mechanism. As defined herein, computer-readable storage media and communications media are mutually exclusive.

The memory 118 may store instructions that cause the computing device 104 to receive an indication of a digital file 102 such as, for example, file 1. The indication may be received in response to input generated on an input device by a user. For example, the input may be the user selecting an icon representing the digital file 102 on a display screen or typing the name of the digital file 102 on a keyboard. The indication received by the computing device 104 may be an electrical signal. Once the digital file 102 is identified to the computing device 104, the computing device 104 may identify a sequence of DNA nucleotides that is an ID sequence for the digital file 102. For example, instructions stored in the memory 118 may cause the computing device 104 to access a lookup table that correlates the identity of a digital file 102 with the particular string of As, Gs, Cs, and Ts. As described in greater detail below, this ID sequence may be present on DNA strands that contain data from the digital file 102. The computing device 104 may also receive an indication of a sequencing technique. In one implementation, this indication is received as an electrical signal generated in response to input from a user to an input device. For example, the selected sequencing technique may be Illumina® sequencing by synthesis, SMRT sequencing, SOLiD sequencing, 454 sequencing, etc.

Instructions stored in the memory 118 may cause the computing device 104 to identify an end sequence of the sequencing adaptor used in the selected sequencing technique. In one implementation, the memory 118 may store sequences of the different types of sequencing adaptors that may be used for the various options for sequencing techniques. The end sequence may also be predefined and stored. In one implementation, the user may select a desired length of overlap (e.g., 20 nt) and the computing device 104 may identify a sequence at the end of the sequencing adaptor that matches the desired length. The computing device 104 using instructions in the memory 118 and the processing unit(s) 116 may design a staple that is complementary in part to the ID sequence and complementary in part to the end sequence of the sequencing adaptor. The computing device 104 may send the staple sequence along with instructions to synthesize oligonucleotides having the sequence to the oligonucleotide synthesizer 106. The sequencing adaptors may similarly be created by instructions sent from the computing device 104 to the oligonucleotide synthesizer 106. Additionally or alternatively, the sequencing adaptors may be obtained from a pre-existing store of those molecules. For example, a sequencing-by-synthesis procedure may use a first sequencing adaptor that includes a first sequencing adaptor sequence (e.g., 29 nt in length) directly adjacent to a first sequencing primer binding region (e.g., 33 nt in length) and a second sequencing adaptor that includes a second sequencing adaptor sequence directly adjacent to a second sequencing primer binding region. The first sequencing adaptor sequence and the second sequencing adaptor sequence may hybridize to DNA sequences attached to a flowcell used for the sequencing-by-synthesis sequencer.

The memory 118 may include instructions that cause the system 100 to combine all or part of a DNA pool 110 with the staples and the sequencing adaptors. In implementations, the combination may be performed by one or more robotics/microfluidic systems 120. The system 100 may also send instructions to ligate the DNA strands which encode a portion of the digital file 102 to the sequencing adaptors. These instructions may, for example, take the form of instructions to the robotics/microfluidic system 120 to add DNA ligase to the DNA pool 110 that includes the staples and sequencing adaptors. The computing device 104 responding to instructions from the memory 118 may receive DNA sequencer read data from the DNA sequencer 112 and identify reads within the DNA sequencer read data that encode a portion of the digital file 102. The reads may be identified at least in part based on the presence of the ID sequence within those reads.

The one or more robotics/microfluidics system 120 may interface with one or more of the computing device 104, the oligonucleotide synthesizer 106, the DNA storage library 108, the DNA sequencer 112, and the PCR thermocycler 114 via a one or more direct or networked connections that may be wired or wireless connections. The robotics/microfluidics system 120 may control operation of the oligonucleotide synthesizer 106, the DNA sequencer 112, and the PCR thermocycler 114 as well as move samples through different stages of system 100 to create a fully or partially automated system.

The one or more robotics/microfluidics system 120 may include one or more robotic devices such as, for example, Andrew liquid handling robot (Andrew Alliance, Geneva Switzerland) or the SOLO™ liquid handler (Hudson Robotics, Springfield N.J.), etc.

Microfluidics is a multidisciplinary field intersecting engineering, physics, chemistry, biochemistry, nanotechnology, and biotechnology, with practical applications to the design of systems in which small volumes of fluids will be handled. Typically, fluids are moved, mixed, separated, or otherwise processed. Numerous applications employ passive fluid control techniques like capillary forces. In some applications, external actuation is additionally used for a directed transport of the media. Examples of external actuation include rotary drives applying centrifugal forces for the fluid transport on the passive chips. Active microfluidics refers to the defined manipulation of the working fluid by active (micro) components such as micropumps or micro valves. Micro pumps supply fluids in a continuous manner or are used for dosing. Micro valves determine the flow direction or the mode of movement of pumped liquids. Often processes which are normally carried out in a lab are miniaturized on a single chip in order to enhance efficiency and mobility as well as reduce sample and reagent volumes.

For example, the robotics/microfluidics system 120 may be configured to move a volume of liquid from a first chamber to a second chamber in response to a series of instructions from the computing device 104. One type of manipulation is sample partitioning. Numerous methods can be used to divide samples into discrete partitions (e.g., droplets). Examples of partitioning methods and systems include use of one or more of emulsification, droplet actuation, microfluidics platforms, continuous-flow microfluidics, reagent immobilization, and combinations thereof. In some embodiments, partitioning is performed to divide a sample into a sufficient number of partitions such that each partition contains one or zero nucleic acid molecules. In some embodiments, the number and size of partitions is based on the concentration and volume of the bulk sample.

Microfluidics systems and methods to divide a bulk volume into partitions include emulsification, generation of "water-in-oil" droplets, and generation of monodisperse droplets as well as using channels, valves, and pumps. Partitioning methods can be augmented with droplet manipulation techniques, including electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). In some embodiments, a droplet microactuator is supplemented with a microfluidics platform (e.g. continuous flow components). Some implementations of microfluidics systems use a droplet microactuator. A droplet microactuator can be capable of effecting droplet manipulation or operations, such as dispensing, splitting, transporting, merging, mixing, agitating, and the like.

Figure 2:
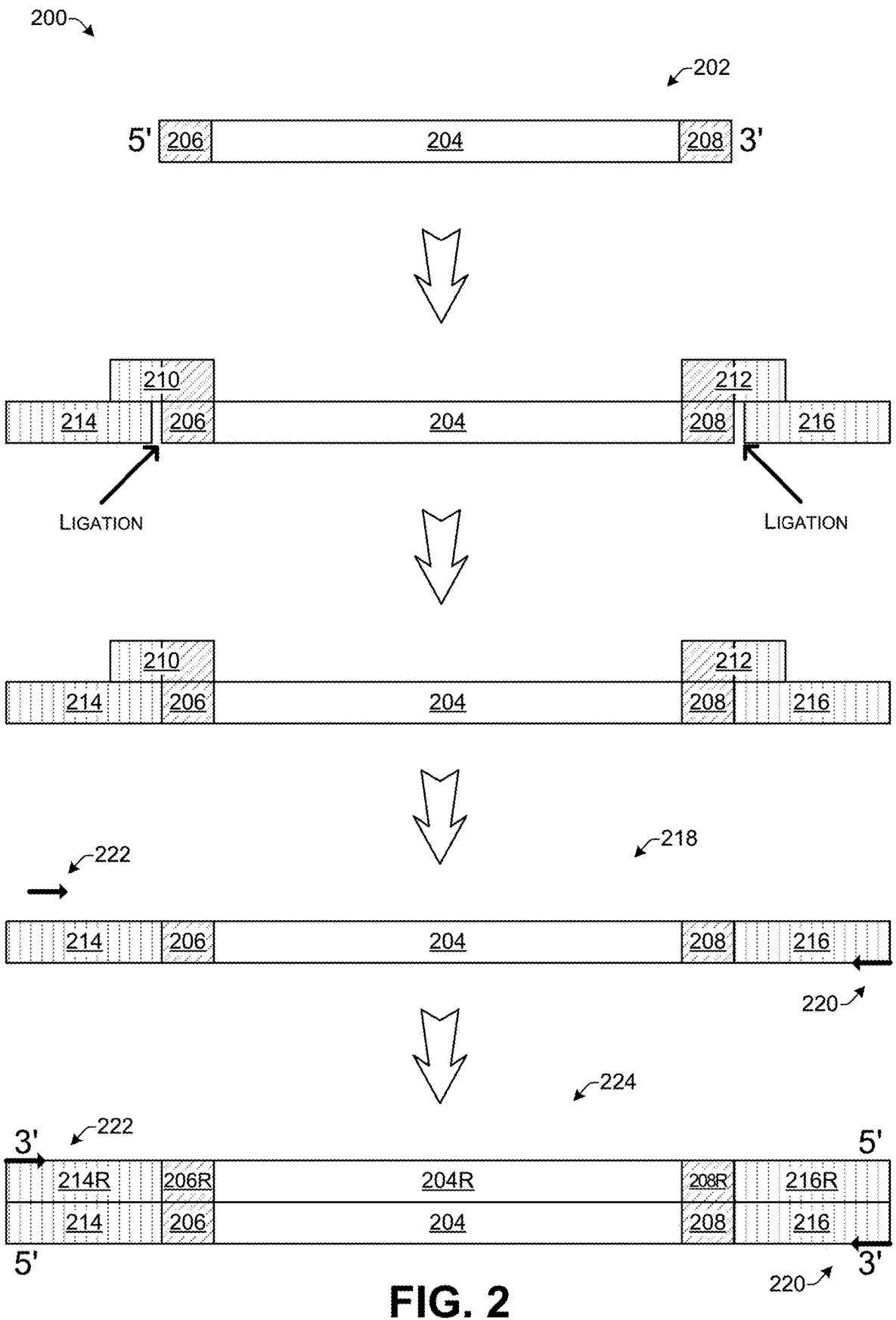
FIG. 2 shows a schematic representation of attaching sequencing adaptors to a DNA strand using staples.

FIG. 2 shows a schematic implementation 200 of a technique for using ligation to add sequencing adaptors. DNA strand 202 is an example of a DNA strand that may be present in a DNA pool 110. The middle of the DNA strand 202 is a payload sequence 204 that contains nucleotides encoding data corresponding to a portion of a digital file 102. The payload sequence 204 is flanked by a 5'-end sequence 206 and a 3'-end sequence 208 that serve as ID sequences or keys for unique identification. Thus, the structure of the DNA strand 202 may be key-data-key. The 5'-end sequence 206 and the 3'-end sequence 208 may have the same or different nucleotide sequences. The size limit of synthetic DNA strands that can be created by oligonucleotide synthesis technology is about 200 nt. This length is expected to increase in the future and the techniques of this disclosure work equally well with DNA strands of different lengths. In an implementation lengths of the end sequences may be between about 15-20 nt. The 5'-end sequence 206 and the 3'-end sequence may be the same or different in length. Thus, depending on the oligonucleotide synthesis technology, the length of the payload sequence 204 may be between about 160-170 nt. Other lengths and other ratios of the key to data regions are also possible. As the length of the ID sequence/key increases there is a greater variety of ID sequences that may be used to uniquely label DNA strands, but there is less of the DNA strand available for the payload sequence 204.

The uniqueness of the 5'-end sequence 206 and the 3'-end sequence 208 may be used to identify any characteristic associated with the data in the payload sequence 204. For example, each unique DNA strand may be associated with a unique ID sequence. Doing so would lead to a very high number of ID sequences being necessary to retrieve a large number of DNA strands. In one implementation, each ID sequence may be associated with a digital file 102 so that every payload sequence 204 encoding data from that digital file 102 is flanked by the same unique ID sequences. This is the implementation that will be discussed through the remainder of this disclosure; however, DNA strands and techniques discussed herein are equally applicable to other relationships between the ID sequences and the encoded data. As an example, the ID sequences may be associated with sets of digital files 102 (e.g., all the files in a "folder," all email sent by "John Smith," all videos generated on Oct. 1, 2016, etc.) so that retrieving all DNA strands with a given set of ID sequences leads to retrieving data that is associated with more than one digital file 102.

The 5'-end sequence 206 and the 3'-end sequence 208 may be PCR primer sites that are used to selectively amplify only those DNA strands with those primer sites. By assigning different primers to different payload sequences 204 it is possible to select a subset of DNA strands from the DNA pool 110. Random access can be provided by mapping the ID sequence to PCR primers, which are then used in a PCR amplification reaction performed by the PCR thermal cycler 114 that amplifies only the strands with the desired data. To read a particular ID sequence's value from the solution, PCR is performed using that ID sequence's primer, which amplifies the selected strands. The sequencing process then reads only those strands, rather than the entire DNA pool 110. This technique for achieving random access of DNA strands in a DNA pool 110 is described in greater detail elsewhere such as in U.S. Provisional Patent App. No. 62/255,269.

The techniques of this disclosure proceed differently by using short DNA "staple" molecules 210 and 212 that hybridize in part with the ID sequences (end sequences 206, 208) of the DNA strand 202 and that hybridize in part with the sequencing adaptors 214 and 216. The 5'-end staple 210 holds the DNA strand 202 adjacent to a first sequencing adaptor 214 and the 3'-end staple 212 holds the DNA strand 202 adjacent to a second sequencing adaptor 216. Thus the label "staple." DNA staples are also used in DNA origami. DNA origami is the nanoscale folding of DNA to create non-arbitrary two- and three-dimensional shapes at the nanoscale. The specificity of the interactions between complementary base pairs make DNA a useful construction material, through design of its nucleotide sequences. The process of DNA origami involves the folding of a long single strand of DNA aided by multiple smaller "staple" strands. These shorter strands bind the longer strand in various places, resulting in various shapes. Although this disclosure is not directed to folding DNA strands into various shapes, the function and use of staple strands is similar.

The length of overlap between the staples 210 and 212 and the DNA strand 202 may in one implementation be about 15-20 nt. Similarly, the length of overlap between the staples 210 and 212 and the sequencing adaptors 214, 216 may also be about 15-20 nt. Thus, in one implementation the staples 210, 212 may be about 30-40 nt. The division between the portion of a staple 210, 212 that overlaps with the DNA strand 202 and a portion that overlaps with a sequencing adaptor 214, 216, may be at the middle of the staple 210, 212 or at some other point.

Once the sequencing adaptors 214, 216 and the DNA strand 202 are all attached to the staples 210, 212, DNA ligase may be used to covalently bond the DNA backbone of the sequencing adaptors 214, 216 to the DNA strand 202. DNA ligase is a specific type of enzyme, a ligase, that facilitates the joining of DNA strands together by catalyzing the formation of a phosphodiester bond. The mechanism of DNA ligase is to form two covalent phosphodiester bonds between 3' hydroxyl ends of one nucleotide, ("acceptor") with the 5' phosphate end of another ("donor"). Ligation uses a 5' phosphate which can be added to the molecules when they are synthesized by the oligonucleotide synthesizer 106 or added by treating the DNA with a kinase such as T4 polynucleotide kinase. A co-factor is generally involved in the reaction, and this is usually ATP or NAD$^+$. Any type of DNA ligase may be used such as *E. coli* DNA ligase, DNA ligase from bacteriophage T4, thermostable ligase from thermophilic bacteria, mammalian ligase, or the like. For optimal ligation efficiency with cohesive-ended fragments such as created by the use of staples with overhangs, the optimal enzyme temperature (e.g., 37° C. for T4 DNA ligase) is balanced with the melting temperature $T_m$ of the strands being ligated. Hybridization between the staples 210, 212 and the DNA strand 202 plus the sequencing adaptors 214, 216 will not be stable if the temperature is high enough to disrupt hydrogen bonding between the DNA strands. A ligation reaction is most efficient when the DNA strands are already stably annealed, and disruption of the annealing ends would therefore result in low ligation efficiency. In general, the shorter the overhang, the lower the $T_m$.

Following ligation, the "nicks" between the sequencing adaptors 214, 216 and the DNA strand 202 are sealed. Sealing the nicks creates a ligation product 218 that is a single DNA strand which includes the original DNA strand 202 and the sequencing adaptors 214, 216. This ligation product 218 is now ready for sequencing by a sequencing technique compatible with the sequencing adaptors 214, 216.

Processing on the level of the DNA strands may stop once the DNA sequencer 112 has received the ligation products 218 and generated sequencing reads. However, in one implementation the ligation products 218 may be amplified by PCR prior to sequencing. Amplification increases the number of copies of each ligation product 218 which provides the DNA sequencer 112 with more molecules to analyze and may result in more accurate sequencing reads. In an implementation that uses PCR, a forward PCR primer 220 is introduced that binds to the 3' end of a single strand of the ligation product 218. Following ligation, the ligation product 218 may exist only as ssDNA without a complementary strand. Due to the directionality of DNA polymerase, creation of a complementary strand during PCR proceeds from the 3' end of a DNA strand to the 5' end. Thus, a reverse primer 222 designed to amplify a DNA strand that is complementary to the single-stranded ligation product 218 will not have a binding site until the complementary DNA strand is synthesized.

During PCR amplification a reverse-complementary DNA strand is synthesized from the ligation product 218. This molecule includes a reverse complement of the payload sequence 204R, a reverse complement of the 5'-end sequence 206R, a reverse complement of the 3'-end sequence 208R, the reverse complement of the first sequencing adaptor 214R, and the reverse complement of the second sequencing adaptor 216R. Both the forward and reverse strands of the ligation product form a double stranded DNA strand 224. Both the forward primer 220 and the reverse primer 222 are designed to be complementary to the ends of the double-stranded DNA strand 224. This provides for PCR amplification of the full length of the ligation product 218 which results in multiple copies that all include the entirety of the first sequencing adaptor 214 and the second sequencing adaptor 216. Thus, in one implementation, the sequences of the PCR primers are dictated by the sequence of the sequencing adaptors 214, 216. This makes it possible for the same primers 220, 222 to be used for amplification of multiple different DNA strands even DNA strands that include dissimilar end sequences 206, 208 so long as ligation has the same sequencing adaptors 214, 216 to the ends of the DNA strands. Thus, PCR may be used to amplify payload sequences 204 that correspond to multiple different files simultaneously and uniformly because the same primers 220, 222 are used.

Note that unmodified staples 210, 212 can work as primers in this PCR enrichment, which can lead to unpredictable PCR bias. To avoid this, the staples 210, 212 can be either removed before PCR using a size selective gel or chemically modified in the 3' end to avoid strand extension during PCR. This leaves the primers 220, 222 as the only places for PCR amplification to occur.

As PCR proceeds, the number of copies of both strands of the dsDNA strand 224 will increase. The reverse-complementary DNA strand may be ignored by the DNA sequencer 112 because it does not include the sequencing adaptors 214, 216 but rather includes sequences that are the reverse complement of those sequencing adaptors. Thus, the reverse-complement DNA strand functions as a template for making more copies of the ligation product 218 during PCR. Thus—unlike other random access techniques that use PCR primers which hybridize to the end sequences 206, 208 of a DNA strand 202—this technique uses the addition of sequencing adaptors 214, 216 by ligation to achieve random access while the use of PCR in PCR primers increases the number of copies of those DNA strands that already include the sequencing adaptors 214, 216.

Figure 3:
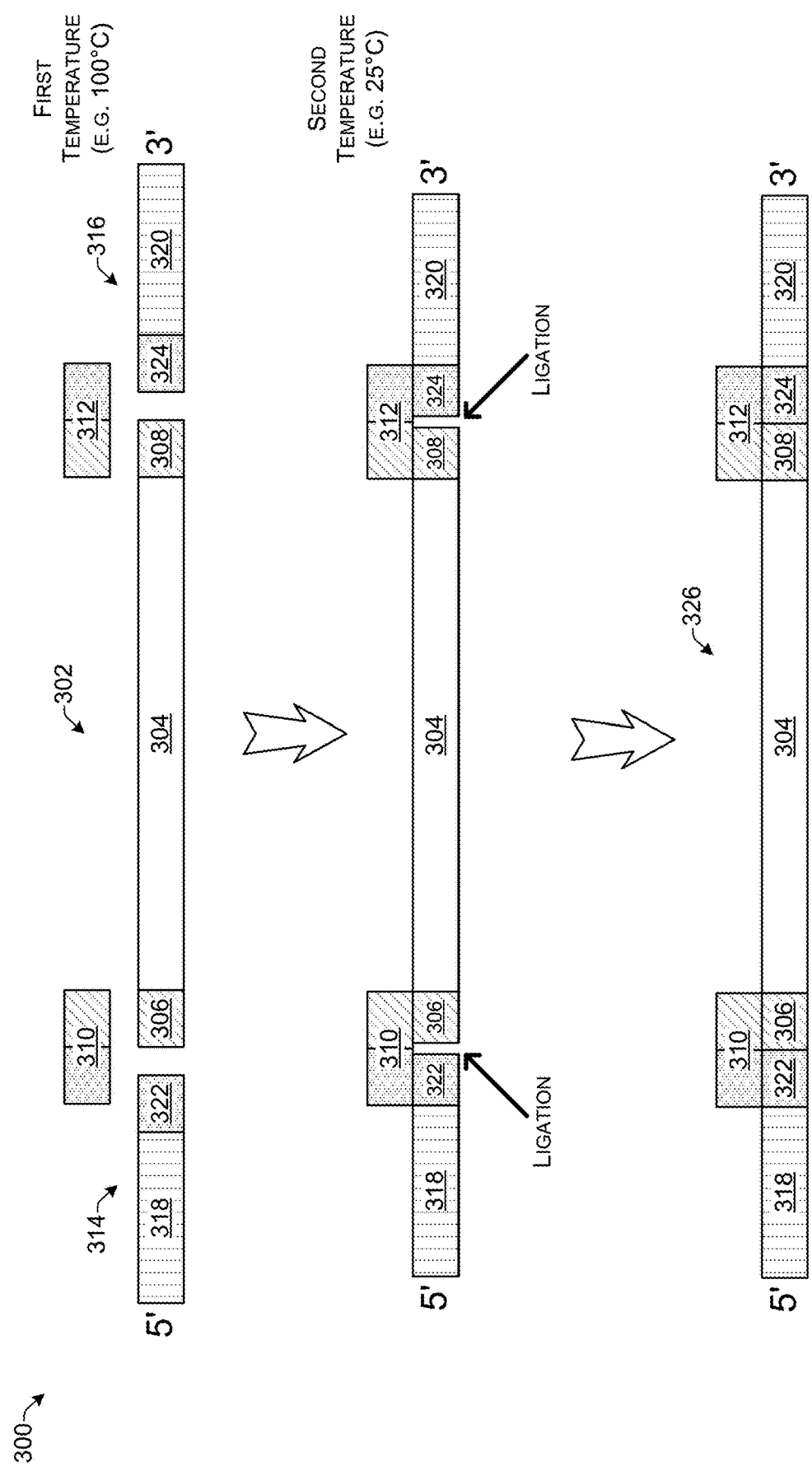
FIG. 3 shows a schematic representation of attaching sequencing adaptors modified with a region that is complementary to a staple to a DNA strand using staples.

FIG. 3 shows a schematic implementation 300 of a technique for using ligation to add sequencing adaptors. Similar to the technique introduced in FIG. 2, a DNA strand 302 includes a payload sequence 304, a 5'-end sequence 306, and a 3'-end sequence 308. Staple molecules 310, 312 function the same as described above in FIG. 2. The sequencing adaptors 314, 316 that include the sequencing adaptor sequences 318, 320 are different. Rather than being only the sequencing adaptor sequences themselves as in FIG. 2, these sequencing adaptors 314, 316 also include an additional "staple match sequence" 322, 324 that hybridizes to a portion of the respective staple 310, 312. This allows for ligation of the sequencing adaptor sequences 318, 320 to the DNA strand 302 without staples 310, 312 hybridizing to a portion of the sequencing adaptors 318, 320 themselves. This may be beneficial if, for example, the sequences of the sequencing adaptors 318, 320 are not conducive to hybridization to a complementary DNA strand under the reaction conditions that will be used for processing. Additionally, this technique may allow for a greater level of modularity and suitability for automation because the same staples 310, 312 may be used for any given pair of ID sequences (5'-end sequence 306, 3'-end sequence 308) based on the ability to hybridize with the staple match sequences 322, 324 no matter which type of sequencing adaptor sequence 318, 320 is present. Thus, in one implementation, different versions of the sequencing adaptors 314, 316 may be prepared such that each different version has a sequencing adaptor sequence 318, 320 for a different sequencing technique but all share the same staple match sequences 322, 324.

Annealing between the DNA strand 302, the staples 310, 312, and the molecule that includes the sequencing adaptors 314, 316 (or the sequencing adaptors 214, 216 without the staple match sequences as shown in FIG. 2) may be made more specific by following a gradual cooling ramp. By gradually lowering the temperature from a first, warmer temperature to a second, cooler temperature the staples 310, 312 are more likely to anneal to the correct target site because there is greater specificity for annealing at higher temperatures. For example, the cooling ramp may proceed from a first temperature of around 100° C. in which all of the various DNA strands are separate to a lower temperature of around 25° C. in which the staples 310, 212 have partially annealed to the DNA strand 302 and to the molecules that include the sequencing adaptors 314, 316. The temperature changes may be effectuated by any technique that can change the temperature of the DNA strands and the media in which they are contained. In one implementation, the PCR thermocycler 114 may be used to control the temperature. Thus in practice, a DNA pool 110 or portion thereof may be placed into the PCR thermocycler 114 in order to achieve specific temperatures and implement a cooling ramp whether or not PCR is used to selectively amplify DNA.

In one implementation, cooling the first temperature to the second temperature are performed slowly over the course of about one hour. At the higher temperature of, for example around 100° C., the respective DNA strands are not able to anneal due to the high temperature. As the temperature is gradually lowered, the most thermodynamically favorable annealing happens first which is typically annealing between complementary strands that exactly match each other. Thus, a slow cooling process from a first temperature to a second temperature increases the specificity of annealing which increases the probability that the staples 310, 312 will anneal to the complementary regions of the 5'-end sequence 306, 3'-end sequence 308, and the staple match sequences 322, 324.

Ligation may be performed following cooling to the second, lower temperature. In an implementation the temperature may be raised to a different, third temperature that is the most efficient temperature for the DNA ligase to operate such as, for example, 37° C. for T4 DNA ligase. Ligation creates a ligation product 326 that includes the payload sequence 304, the end sequences 306, 308 that function as unique ID sequences, the staple match sequences 322, 324, and sequencing adaptor sequences 318, 320. This is similar to the ligation product 218 shown in FIG. 2.

Even if the staples 310, 312 form secondary structures or nonspecific annealing, this is unlikely to negatively affect the read output generated by the DNA sequencer 112. Secondary structures can include hairpins, self-dimers, and cross-dimers. Nonspecific annealing of staples 310, 312 to a location such as, for example, a payload sequence 304 will not create the structure necessary to position the molecules that include the sequencing adaptors 314, 316 (or the sequencing adaptors 214, 216 of FIG. 2) in a position in which ligation is possible. DNA strands provided to the DNA sequencer 112 that do not have the appropriate sequencing adaptor sequences 318, 320 on the 5'- and 3'-ends will not be sequenced. Thus, mistaken annealing will not affect the accuracy of the sequence of the ligation product 326. Additionally, an excess of staples 310, 312 may be added to a reaction mixture so that there is an abundance of staples 310, 312 to anneal to the other DNA strands. Any staples 310, 312 that remain annealed to the ligation product 326 during sequencing are displaced as part of the sequencing process.

Figure 4:
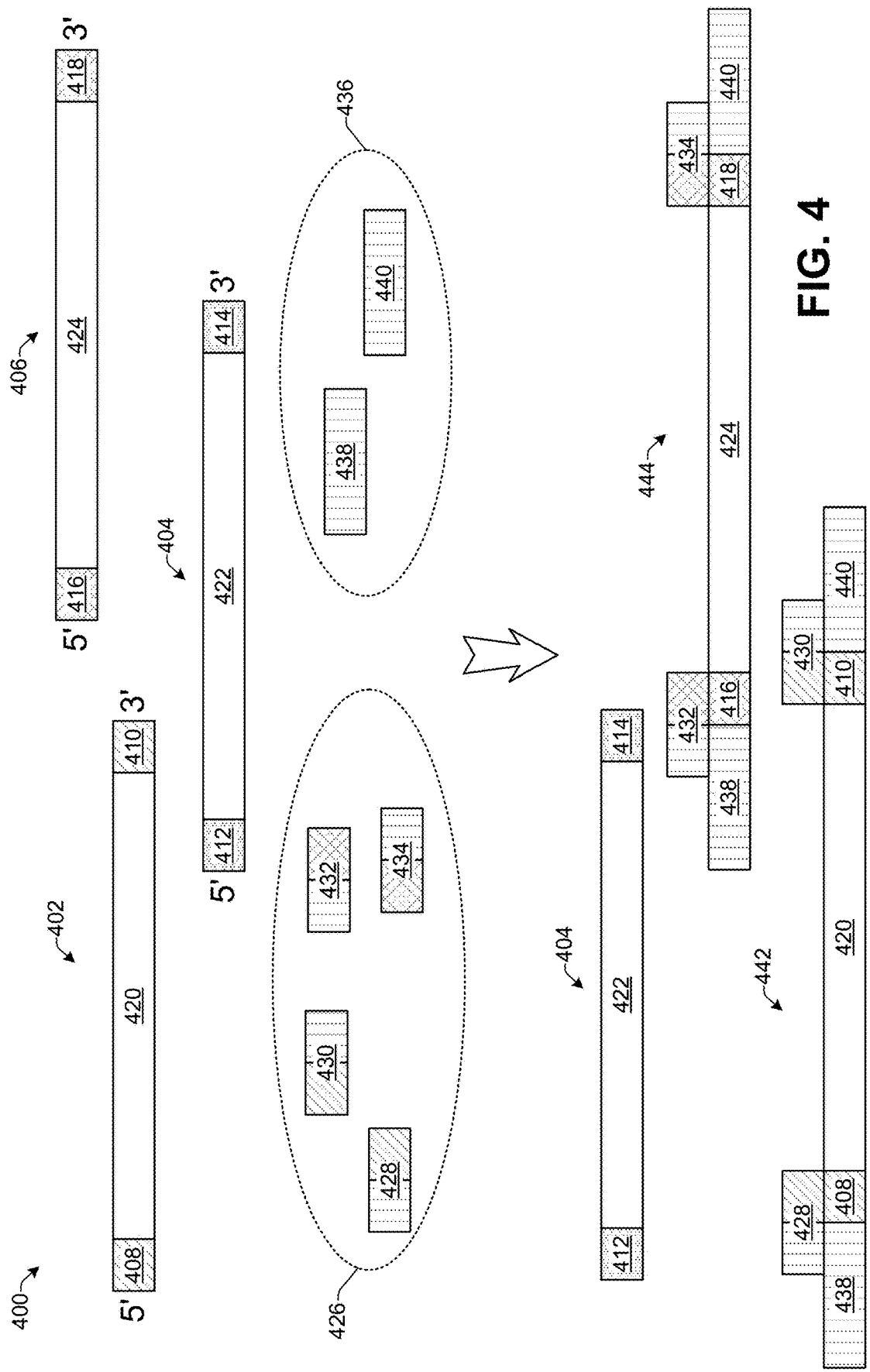
FIG. 4 shows selectively adding sequencing adaptors only to certain DNA strands.

FIG. 4 shows a schematic representation 400 of a technique for using ligation to selectively add sequencing adaptors to certain DNA strands based on ID sequences. This schematic representation 400 uses the same general format as the schematic implementations 200 and 300 shown in FIG. 2 and FIG. 3. Recall that the DNA pool 110 may include multiple DNA strands 402, 404, 406 individual ones of which are associated with data from different digital files 102. These various DNA strands 402, 404, 406 may be mixed within the DNA pool 110 and may be differentiated by ID sequences 408, 410, 412, 414, 416, 418, on the 5'-ends and 3'-ends of the DNA strands 402, 404, 406.

DNA strand 402 includes a payload sequence 420 from a first digital file that is flanked by a 5'-end sequence 408 and a 3'-end sequence 410. DNA strand 404 includes a payload sequence 422 from a second digital file that is flanked by a 5'-end sequence 412 and a 3'-end sequence 414. DNA strand 406 includes a payload sequence 424 from a third digital file which is flanked by a 5'-end sequence 416 and a 3'-end sequence 418. Each of these payload sequences 420, 422, 424 may be (but do not necessarily have to be) different because they include different portions of different digital files. However, the respective end sequences 408, 410, 412, 414, 416, 418, are sufficiently different to allow for discrimination of each DNA strand 402, 404, 406 from others that do not share the same end sequence.

The DNA strands 402, 404, 406 may be combined with a set of staples 426 that includes multiple pairs of staples which may bind to some but less than all of the DNA strands 402, 404, 406. Here, a first staple 428 can anneal in part to the 5'-end sequence 408 of DNA strand 402 and a second staple 430 can anneal to the 3'-end sequence 410. Similarly, a third staple 432 can anneal to the 5'-end sequence 416 of DNA strand 406 while a fourth staple 434 can anneal to the 3'-end sequence 418. In this example, there are no staples that anneal to the end sequences of DNA strand 404. Random access is achieved by the choice of which staple sequences to combine with the DNA strands in the DNA pool 110. Thus, it is possible to use combinations of the set of staples 426 that can anneal to DNA strands associated with more than one digital file. Differences in the sequences of the staples 428, 430, 432, 434 cause the staples to anneal to the complementary regions of the DNA strands 402, 404, 406. Slowly cooling a mixture that includes both the DNA strands 402, 404, 406, the set of staples 426, and a pair of sequencing adaptors 436 from a first higher temperature at which annealing will not occur to a lower temperature at which annealing can occur enhances annealing specificity. The number of different staple sequences that can be effectively differentiated by annealing provides the number of unique IDs or keys that may be assigned to a given DNA pool 110.

The number of possible unique IDs is represented by the concept of "address space." Address space is an indication of a number of different end sequences that may be created which in turn identifies how many separate digital files 102 or other groupings of information may be uniquely labeled within a single DNA pool 110. Address space is primarily limited by the number of nucleotides used to generate an ID sequence. As discussed above, the end sequences 408, 410, 412, 414, 416, 418, may be any length but in some implementations are 15-20 nt. The maximum address space given a four-letter alphabet (i.e., A, G, C, T) is $4^n$ where n is the length of the sequence used for identification. So with an ID sequence of 15 nt, the theoretical maximum address space is $4^{15}$ or 1,073,741,824. All sequences that, for whatever reason, cannot function as end sequences, or whose complement cannot function as a portion of a staple sequence, are excluded and the remaining number is the address space for an ID sequence of length n. Sequences that form secondary structures may be excluded to avoid end sequences that anneal to payload sequences, staples that fold back on themselves, etc. For example, all staples can have secondary structures with more than six base self-pairing may be excluded due to a tendency to form long-stem hairpin structures. Highly similar sequences (e.g. in terms of Hamming distance) could also be excluded to avoid mistaken annealing that results in retrieval of the wrong file.

The sequence space for staples is much larger than that for PCR primers performing the role of providing random access. The design of primers must be concerned with nonspecific annealing to regions of the DNA strands such as the payload areas. Although software exists to design primers that have similar $T_m$, avoid secondary structures, and avoid nonspecific binding, the exclusion of these potential primer sequences greatly limits the sequence space. However, with staples, nonspecific annealing that does not lead to ligation of a sequencing adaptor does not negatively impact the results of sequencing. Additionally, the concerns related to melting temperature, $T_m$, are less for staple design than for primer design because of the use of a cooling ramp. Primers with melting temperatures in the range of 52-58° C. generally produce the best results. Primers with melting temperatures above 65° C. have a tendency for secondary annealing. Primers with even weak secondary structures (e.g., three base self-pairing) can have an effect on PCR efficiency because the secondary structures can form kinetic traps which reduce primer hybridization during the relatively short (e.g., less than one minute) hybridization step. Kinetic traps are a much smaller concern for staples because of the relatively slow cooling ramp. All primers used during the same PCR reaction should have approximately the same $T_m$. However, when staples are used particularly with the process that incorporates a cooling ramp, a variety of staples with a range of different $T_m$ may be used together.

The pair of sequencing adaptors 436 is also combined with the DNA strands 402, 404, 406 and the set of staples 426. The pair of sequencing adaptors 436 includes a first sequencing adaptor 438 and a second sequencing adaptor 440. Depending on the specifics of the sequencing technology used, the first sequencing adaptor 438 and the second sequencing adaptor 440 may both have flowcell binding sites that bind to complementary sequences attached to a flowcell in the DNA sequencer 112. Note that two staples (e.g., 428, 432) which are complementary in part to different end sequences are also both complementary in part to the same sequencing adaptor (e.g., 438). Thus, the discrimination between different DNA strands 402, 404, 406 is achieved by the staples rather than the sequencing adaptors 438, 440.

Following annealing and ligation, the DNA strand 404 remains unmodified because none of the set of staples 426 include portions that anneal to the 5'-end sequence 412 and the 3'-end sequence 414. The DNA strand 402 is ligated to the sequencing adaptors 438, 440 by use of the corresponding staples 428, 430. This creates a first ligation product 442 that makes it possible to sequence the payload sequence 420. Similarly, DNA strand 406 is ligated to the sequencing adaptors 438, 440 by use of the corresponding staples 432, 434. This creates a second ligation product 444 that makes it possible to sequence the payload sequence 424. It is to be understood that in typical reaction conditions there will be many thousands or millions of each type of molecule interacting with each other ultimately resulting in a large number of ligation products 442, 444.

Each of the ligation products 442, 444 may be sequenced by the DNA sequencer 112. The ligation products 442, 444 have the same sequencing adaptors 438, 440 on the ends, so the ligation products 442, 444 will be processed the same by the DNA sequencer 112. Thus, in instances in which DNA strands corresponding to digital data from multiple different files are sequenced together by the DNA sequencer 112, the data corresponding to each of the separate multiple different files is separated from the other digital file data after sequencing. The separation is done on the basis of the read sequences output by the DNA sequencer 112. Sequencing captures nucleotide sequences between the sequence adaptors 438, 440 so the output from the DNA sequencer 112 also includes the nucleotide sequences of the respective 5'-end sequences 408, 416 and the respective 3'-end sequences 410, 418 of the sequence ligation products 442, 444. Thus, the different sequences found in the end sequences may be used for in silico analysis to separate sequencing reads that originated from DNA strand 402 from those that originated from DNA strand 406. After the in silico separation, the respective pieces of different digital files may be recombined according to techniques described elsewhere.

Figure 5:
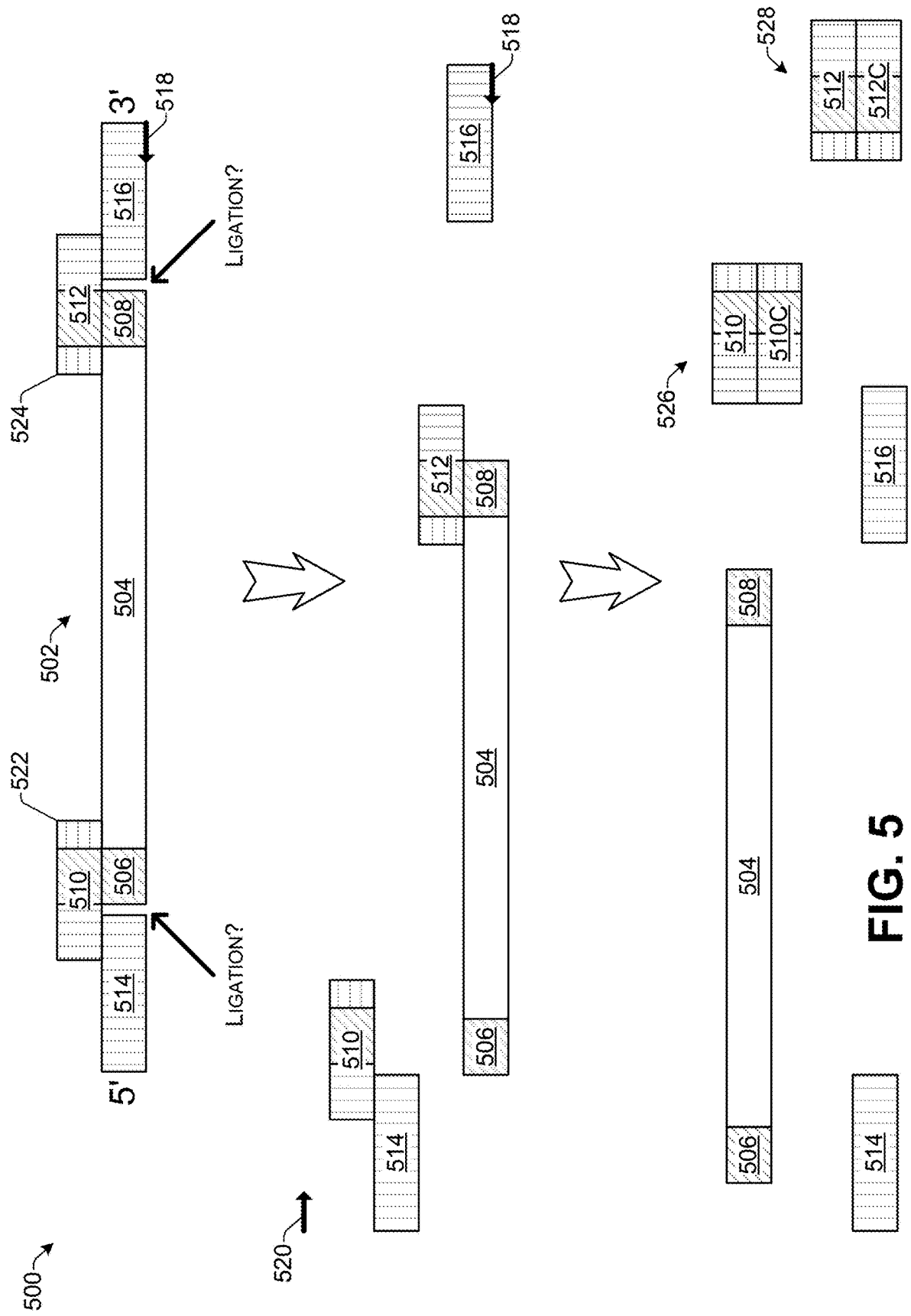
FIG. 5 shows use of complementary short sequences to prevent staples from acting as PCR amplification sites.

FIG. 5 shows a schematic representation 500 of how staple match sequences may be used to prevent staples from acting as PCR amplification sites. During implementations in which ligation products are amplified by PCR, the staples themselves as well as PCR primers may be starting points for overlap-extension PCR (OE-PCR). This type of PCR is also called "Splicing by Overlap Extension" or SOEing.

DNA ligase is not 100% efficient. There are some nicks between DNA strands that are not joined with DNA ligase. Thus, with a population of a very large number of different DNA strands, staples, and sequencing adaptors there will be some in which ligation does not occur or does not occur fully. As described previously, a DNA strand 502 with a payload sequence 504, a 5'-end sequence 506, and a 3'-end sequence 508 may anneal to a portion of a first staple 510 and to a portion of a second staple 512. A first sequencing adaptor 514 may anneal to a portion of the first staple 510 and a second sequencing adaptor 516 may anneal to a portion of the second staple 512. If ligation proceeds completely, a ligation product as illustrated in FIGS. 2-4 will result. However, for those DNA strands in which ligation does not occur at one or more potential ligation sites alternative annealing may create unwanted side products.

Unwanted side products may include structures such as the first staple 510 annealed to the first sequencing adaptor 514, the DNA strand 502 annealed to the second staple 512, the second sequencing adaptor 516 annealed to a sequencing primer 518, etc. OE-PCR will proceed in the same reaction mixture together with the desired PCR amplification of full-length ligation products that include both sequencing adaptors 514, 516 and the DNA strand 502. Repeated cycles of PCR in the presence of an excess of the staples 510, 512, the forward primer 518, and the reverse primer 520 may create additional full-length ligation products.

Additional full-length ligation products are not themselves problematic, but the creation of additional full-length ligation products through OE-PCR may occur only for those sets of staples 510, 512 that do not form secondary structures. Staples that do form secondary structures will likely not anneal in a manner that creates a site for initiation of DNA polymerase. Thus, in implementations in which there are multiple different DNA strands with multiple different ID regions (e.g. millions of different DNA sequences functioning as ID regions), the use of a number of different staple pairs, such as illustrated in FIG. 4, it may be possible that some of the staple pairs will enable OE-PCR while others through formation of secondary structures will not. Due to the exponential nature of PCR amplification, this will lead to ever-increasing quantities of the ligation products for which the associated staple pairs can enable OE-PCR. Unequal amounts of PCR amplification introduces a type of PCR bias which will lead to reads from the DNA sequencer 112 that may not accurately reflect the contents of the DNA pool 110. When one file dominates the sequencing reads, the other files will have much lower amount of sequencing reads. The lower amount of sequencing reads may cause payload drop-out and prevent recovery of those files.

In order to prevent OE-PCR and the potential PCR bias, the staples 510, 512 may include an additional non-complementary region 522, 524 that does not anneal to the corresponding location on the DNA strand 502 or to the sequencing adaptor 514, 516. During ligation as normal, these additional non-complementary regions 522, 524 exist as ssDNA hanging to the side of the ligation products. In some implementations, the non-complementary regions 522, 524 may be approximately 15-20 nt long. Of course they may be shorter or longer. Staples illustrated in FIGS. 2-4 are not shown with non-complementary regions but such regions may be present without changing the interactions shown in FIGS. 2-4.

After ligation, the staples 510, 512 may be displaced from the ligation product and inactivated by addition of staple-complement sequences 510C, 512C (i.e. "C" representing complementary) that are the reverse complement of the staples 510, 512 including the non-complementary regions 522, 524. The staple-complement sequences 510C, 512C do not necessarily have to be fully complementary to the staples 510, 512 nor are they required to be exactly the same length. However, the staple-complement sequences 510C, 512C are designed to have a stronger binding energy to the staples 510, 512 than the staples 510, 512 have to the DNA strand 502 and the respective sequencing adaptors 514, 516. Binding energy between two single-stranded DNA strands is approximately proportional to the number of pairing bases. People of ordinary skill in the art will understand how to estimate binding energy through techniques such as the nearest neighbor model and inclusion of interactions between mismatches and neighboring base pairs. Breslauer, et al., *Predicting DNA Duplex Stability from the Base Sequence*. Proceedings of the National Academy of Sciences of the United States of America 83.11 (1986): 3746-3750.

Because the non-complementary regions 522, 524 are complementary to portions of the staple-complement sequences 510C, 512C but are not complementary to sequences available for annealing in the DNA strand 502 or the sequencing adaptors 514, 516, there is a larger number of bases that will pair between the staples 510, 512 and the staple-complement sequences 510C, 512C than between the staples and the standard ligation products. Thus, the greater binding affinity with the staple-complement sequences 510C, 512C will cause the staples to disassociate from the ligation products and form dsDNA products 526, 528 with their complementary sequences. Formation of these dsDNA products 526, 528 prevents the staples 510, 512 from acting as DNA synthesis initiation sites, and thus, prevents OE-PCR products leading to more equal amplification during PCR and reduction of bias that may be introduced by PCR.

In implementations, the staple-complement sequences 510C, 512C may include 3' modifications to avoid these sequences serving as DNA synthesis initiation sites and creating undesired amplification. The 3' modification may be a 3' spacer C3. This modification is a short 3-carbon chain (C3), which is attached to the terminal 3' hydroxyl group of the staple-complement sequence 510C, 512C. The addition of the 3' Spacer C3 can be utilized in a number of molecular methods where a non-nucleoside blocker prevents the 3' end of an oligonucleotide from reacting with an enzyme. Adding this modification to the 3'-end of an oligonucleotide prevents elongation during PCR without noticeably influencing its annealing properties. Vestheim, Hege, and Simon N Jarman. "*Blocking Primers to Enhance PCR Amplification of Rare Sequences in Mixed Samples—a Case Study on Prey DNA in Antarctic Krill Stomachs.*" Frontiers in Zoology 5 (2008): 12.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

Figure 6:
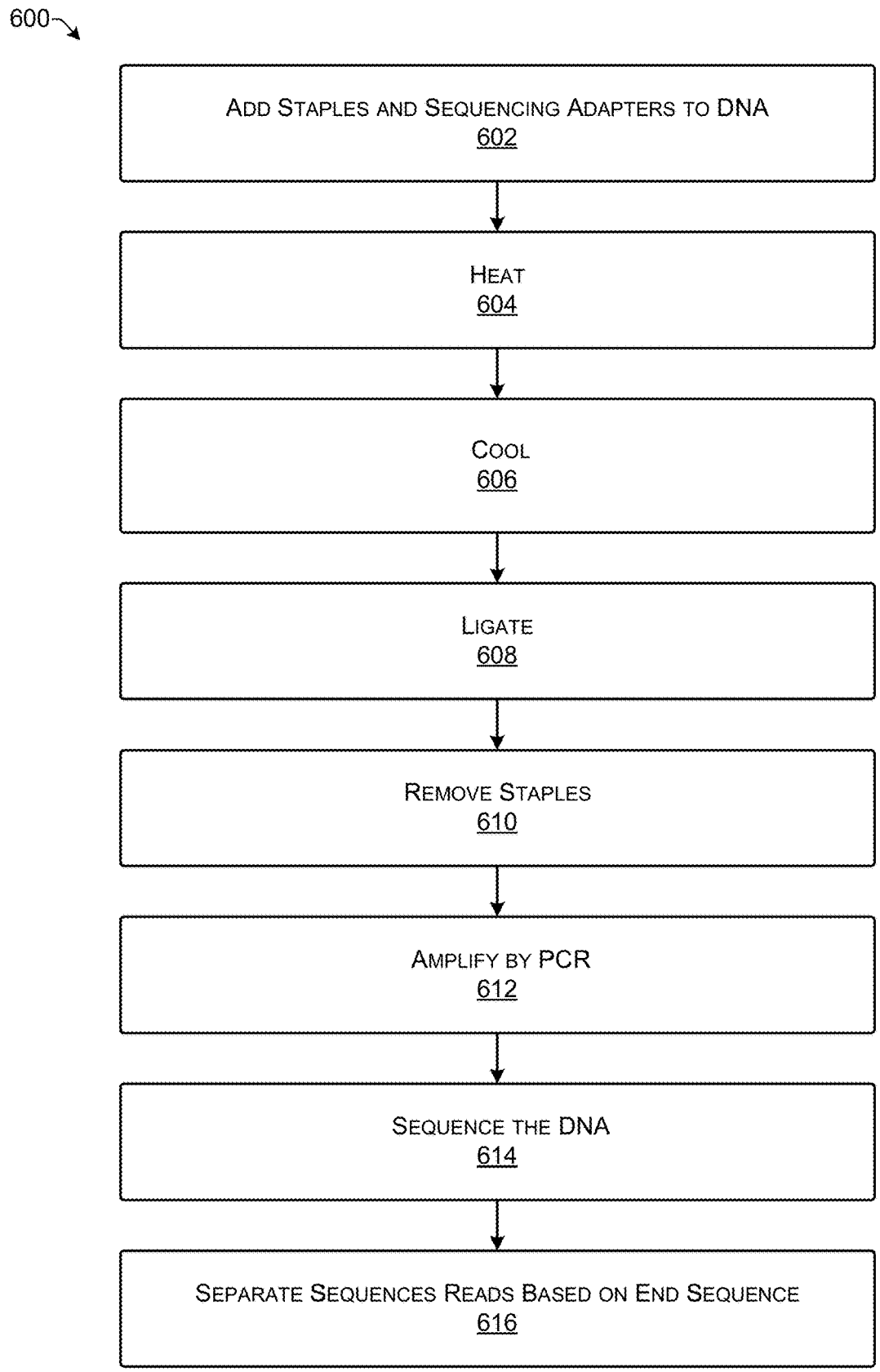
FIG. 6 shows process for selectively adding adaptors to DNA strands.

FIG. 6 shows an illustrative method 600 for randomly accessing DNA strands in a DNA pool. Method 600 may achieve arbitrary, random access on a DNA pool to obtain multiple DNA strands each storing a portion of a same digital file by selectively preparing certain DNA strands for sequencing. The method 600 may be implemented in whole or in part by system 100 shown in FIG. 1. Additionally, portions of method 600 may be understood in view of the schematic representations 200, 300, 400, and 500 shown in FIGS. 2-5.

At 602, one or more staples and one or more sequencing adaptors are added to DNA strands. The DNA strands may be DNA strands in a DNA pool 110 or in a vessel that contains a portion of a DNA pool 110. The staples may be complementary and anneal in part to the DNA strands and in part to the sequencing adaptors. For example, a first staple may be complementary in part to a 5'-end sequence present on the DNA strands and complementary in part to an end sequence a first sequencing adaptor. A second staple may be complementary in part to a 3'-end sequence present on the DNA strands and complementary in part to an end sequence of a second sequencing adaptor. A first sequencing adaptor and a second sequencing adaptor may both be added.

In an implementation, one of the end sequences of the DNA strand may be an ID sequence indicating that nucleotides in a payload sequence of the DNA strand encode a portion of a digital file. The DNA pool may contain multiple DNA strands that all have the same ID sequence but different payload sequences (e.g., when many DNA strands are used to store data from a single digital file).

In an implementation, the sequence adaptors may include staple match sequences that are not typically included on standard sequencing adaptors but are complementary to a part of the staples. In an alternative implementation without staple match sequences, the staples are complementary to a portion of the nucleotides of standard sequencing adaptors.

In an implementation, more than one digital file may be retrieved from the DNA pool at the same time. For example, a third staple that is complementary in part to a second 5'-end sequence present on DNA strands storing a portion of a second digital file and complementary in part to the first sequencing adaptor, and a fourth staple that is complementary in part to a second 3'-end sequence present on the DNA strands storing a portion of the second digital file and complementary in part to the second sequencing adaptor may also be added. This will cause sequencing adaptors to be ligated to DNA strands storing portions of the second digital file as well as the first digital file.

At 604, heat is applied to the DNA strands, staples, and sequencing adaptors. The heat may be applied by heating the vessel or the DNA pool itself. The heat may be applied by using a PCR thermocycler 114 or other heat source. In an implementation, the temperature may be raised to a first temperature at which dsDNA is likely to fully denature. For example, this temperature may be 80° C., 85° C., 90° C., 95° C., 100° C., 105° C., 110° C., 115° C., or another temperature.

At 606, the products which were heated are cooled. This may include cooling the DNA strands, staples, and sequencing adaptors to a second temperature lower than the first temperature. The cooling may be performed by the PCR thermocycler 114 or another cooling device. For example, the second temperature may be room temperature which may be 15° C., 20° C., 25° C., 30° C., 35° C., 40° C., or another temperature.

The change from heating to cooling may be made gradually. For example, a cooling ramp may gradually decrease the temperature from the first, warmer temperature to the second, cooler temperature over a period of time such as, for example, 30 minutes, 40 minutes, 50 minutes, 60 minutes, 70 minutes 80 minutes, 90 minutes, or another period of time. Thus, the rate of cooling may be approximately 2.5° C./min, 1.9° C./min, 1.5° C./min, 1.3° C./min, 1.1° C./min, 0.9° C./min, 0.8° C./min, or a different cooling rate.

At 608, the one or more sequencing adaptors are ligated to the DNA strands. The ligation may be performed by adding a DNA ligase, such as a T4 DNA ligase, *E. coli* DNA ligase, mammalian DNA ligase (I, III, or IV), or other type of DNA ligase to create ligation products. An energy source may also be added such as ATP or $NAD^+$. Ligation joins the phosphate backbone of the DNA strands to the sequencing adaptors creating new, longer DNA strands that are ready for sequencing. In an implementation, DNA ligase may be added only after cooling to the second, lower temperature. The ligation products may include DNA strands having a sequence comprising the first sequencing adaptor, the 5'-end sequence, a payload sequence storing a portion of the digital file, the 3'-end sequence, and the second sequencing adaptor At 610, the staples may be removed prior to PCR amplification. One technique for removing the staples is, after addition of the DNA ligase, addition of a first staple-complement sequence that hybridizes to the first staple with a higher binding energy than the ligation products and a second staple-complement sequence that hybridizes to the second staple with a higher binding energy than the ligation products.

At 612, the DNA strands are amplified by PCR or other amplification technique. The PCR may use at least one primer complementary to a portion of either the first sequencing adaptor or the second sequencing adaptor. The primer may be complementary to an end sequence of the sequencing adaptor that is distal relative to the payload content. In implementations in which the primer only binds to sequences found in the sequencing adaptor, DNA strands without the sequencing adaptor region will not be amplified.

At 614, the DNA strands that are ligated to the sequencing adaptors, the ligation products, are sequenced as described above. The sequencing technique uses the sequencing adaptors that are ligated to the DNA strands. For example, if the sequencing adaptors are for binding to a flowcell in sequencing-by-synthesis then the sequencing technique will use the type of flowcell that binds to the sequencing adaptors.

At 616, DNA sequence read data generated by sequencing is separated based on 3'-end sequence or 5'-end sequence data. This separation may be performed if sequencing adaptors were ligated to DNA strands that respectively correspond to more than one digital file. Thus, sequence reads of the ligation products having a payload sequence storing a portion of a first digital file can be separated from the ligation products having a payload sequence storing a portion of a second digital file.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of performing arbitrary, random access on a DNA pool to obtain multiple DNA strands each storing a portion of a same digital file, the method comprising:
    adding, to a vessel containing DNA strands from the DNA pool:
        a first staple that is complementary in part to a 5'-end sequence present on the multiple DNA strands and complementary in part to a first sequencing adaptor region, the first sequencing adaptor region including a first sequencing adaptor sequence and a first sequencing primer binding region,
        a second staple that is complementary in part to a 3'-end sequence present on the multiple DNA strands and complementary in part to a second sequencing adaptor region, the second sequencing adaptor region including a second sequencing adaptor sequence and a second primer binding region,
    the first sequencing adaptor region, and
    the second sequencing adaptor region;
    heating the vessel to a first temperature;
    cooling the vessel to a second temperature lower than the first temperature; and
    adding, to the vessel, DNA ligase to create ligation products, the ligation products include a subset of the multiple DNA strands, the subset having a sequence comprising the first sequencing adaptor region, the 5'-end sequence, a payload sequence encoding a portion of the digital file, the 3'-end sequence, and the second sequencing adaptor region.

Clause 2. The method of clause 1, wherein the first sequencing adaptor region further includes a staple match sequence and the first staple is complementary in part to the staple match sequence of the first sequencing adaptor region.

Clause 3. The method of clause 1 or 2, wherein the first sequencing adaptor region does not include a staple match sequence and the first staple is complementary in part to the first sequencing adaptor sequence or the first sequencing primer.

Clause 4. The method of any of clauses 1-3, further comprising amplifying the ligation products by polymerase chain reaction (PCR) using at least one primer complementary to a portion of either the first sequencing adaptor region or the second sequencing adaptor region.

Clause 5. The method of any of clauses 1-4, further comprising sequencing the ligation products by a DNA sequencing technique that uses the first sequencing adaptor region and the second sequencing adaptor region.

Clause 6. The method of any of clauses 1-5, further comprising, following the adding DNA ligase, adding a first staple-complement sequence that hybridizes to the first staple with a higher binding energy than the ligation products and a second staple-complement sequence that hybridizes to the second staple with a higher binding energy than the ligation products.

Clause 7. The method of any of clauses 1-6, further comprising:
    adding, to the vessel:
        a third staple that is complementary in part to a second 5'-end sequence present on DNA strands storing a portion of a second digital file and complementary in part to the first sequencing adaptor region, and
        a fourth staple that is complementary in part to a second 3'-end sequence present on the DNA strands storing the portion of the second digital file and complementary in part to the second sequencing adaptor region.

Clause 8. The method of clause 7, further comprising:
    sequencing the ligation products by a sequencing technique that uses the first sequencing adaptor region and the second sequencing adaptor region, wherein the ligation products further include a second subset of the multiple DNA strands, the second subset having a sequence comprising the first sequencing adaptor, the second 5'-end sequence, a payload sequence encoding a portion of the second digital file, the second 3'-end sequence, and the second sequencing adaptor region; and
    separating sequence reads of the ligation products having the payload sequence storing a portion of the first digital file from the ligation products having the payload sequence storing a portion of the second digital file based on at least one of:
        the 5'-end sequence associated with the file and the second 5'-end sequence associated with the second file, or
        the 3'-end sequence associated with the file and the second 3'-end sequence associated with the second file.

Clause 9. A method of selectively preparing a DNA strand for sequencing, the method comprising:
    contacting the DNA strand with a sequencing adaptor;
    contacting the DNA strand with a staple complementary in part to an end sequence of the DNA strand and complementary in part to a first end sequence of the sequencing adaptor; and
    contacting the DNA strand with DNA ligase.

Clause 10. The method of clause 9, wherein the end sequence of the DNA strand is an identification (ID) sequence indicating that nucleotides in a payload sequence of the DNA strand encode a portion of a digital file, wherein a DNA pool contains multiple DNA strands with the same ID sequence but different payload sequences.

Clause 11. The method of clause 9 or 10, further comprising heating the DNA strand to a first temperature and prior to contacting the DNA strand with the DNA ligase, cooling the DNA strand to a second temperature lower than the first temperature.

Clause 12. The method of clause 11, wherein the cooling is performed gradually over about one hour.

Clause 13. The method of any of clauses 9-12, further comprising:
    contacting the DNA strand with a primer complementary to a second end sequence of the sequencing adaptor; and
    amplifying the DNA strand by PCR using the primer.

Clause 14. The method of clause 13, further comprising removing the staple from the DNA strand prior to amplifying the DNA by PCR.

Clause 15. The method of any of clauses 9-14, further comprising sequencing the DNA strand with a DNA sequencing technique that uses the sequencing adaptor.

Clause 16. A system comprising:
    one or more processing units;
    memory coupled to the one or more processing units;
    instructions stored in the memory and executed on the one or more processing units that cause the system to:
        receive an indication of a digital file;
        identify a sequence of DNA nucleotides that is an identification (ID) sequence for the digital file, the ID sequence present on at least one of the 5'-end or the 3'-end of multiple DNA strands that respectively encode one of multiple portions of the digital file;
        receive an indication of a sequencing technique;
        identify an end sequence of a sequencing adaptor used in the sequencing technique; and
        design a staple that is complementary in part to the ID sequence and complementary in part to the end sequence of the sequencing adaptor.

Clause 17. The system of clause 16, wherein the instructions further cause the system to send instructions to an oligonucleotide synthesizer to synthesize multiple copies of the staple.

Clause 18. The system of clause 16 or 17, wherein the instructions further cause the system to send instructions to combine a DNA pool with the staple and the sequencing adaptor, wherein the DNA pool contains the multiple DNA strands that encode a portion of the digital file and other DNA strands encoding portions of one or more different digital files.

Clause 19. The system of any of clauses 16-18, wherein the instructions further cause the system to send instructions to ligate the sequencing adaptor to the DNA strands that encode one of the multiple portions of the digital file.

Clause 20. The system of any of clauses 16-19, wherein the instructions further cause the system to:

receive DNA sequence read data from a DNA sequencer; and identify reads within the DNA sequence read data that encode one of the multiple portions of the digital file based at least in part on the presence of the ID sequence in the reads.

Clause 21. Computer-readable media encoding instructions which when executed by a processing unit cause a computing device to perform the method of any of clauses 1-15.

Clause 22. A system comprising one or more processing units and memory configured to implement the method of any of clauses 1-15.

Clause 23. A system comprising:

means for processing digital information;

means for storing data in memory coupled to the one or more processing units;

means for receiving an indication of a digital file;

means for identifying a sequence of DNA nucleotides that is an identification (ID) sequence for the digital file, the ID sequence present on at least one of the 5'-end or the 3'-end of multiple DNA strands that respectively encode one of multiple portions of the digital file;

means for receiving an indication of a sequencing technique;

means for identifying an end sequence of a sequencing adaptor used in the sequencing technique; and means for designing a staple that is complementary in part to the ID sequence and complementary in part to the end sequence of the sequencing adaptor.

Conclusion

Although the subject matter has been described in language specific to structural features or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context. As used herein in this document "or" means and/or. For example, "A or B" means A without B, B without A, or A and B.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

The invention claimed is:

1. A method of performing arbitrary, random access on a DNA pool to obtain multiple DNA strands each storing a portion of a first digital file, the method comprising:

adding, to a vessel containing the DNA pool, wherein the DNA pool comprises a first subset of DNA strands and a second subset of DNA strands:

a first staple that is complementary in part to a 5'-end sequence present on the first subset of DNA strands and complementary in part to a first sequencing adaptor, the first sequencing adaptor including a first sequencing adaptor sequence, wherein the first staple is not complementary to the second subset of DNA strands, a second staple that is complementary in part to a 3'-end sequence present on the first subset of DNA strands and complementary in part to a second sequencing adaptor, the second sequencing adaptor including a second sequencing adaptor sequence, wherein the second staple is not complementary to the second subset of DNA strands, the first sequencing adaptor, and the second sequencing adaptor;

heating the vessel to a first temperature;

cooling the vessel to a second temperature lower than the first temperature; and adding, to the vessel, DNA ligase to create ligation products, the ligation products having a sequence comprising the first sequencing adaptor, the 5'-end sequence, a payload sequence of the first subset of DNA strands encoding a portion of the first digital file, the 3'-end sequence, and the second sequencing adaptor.

2. The method of claim 1, wherein the first sequencing adaptor further includes a staple match sequence and the first staple is complementary in part to the staple match sequence of the first sequencing adaptor.

3. The method of claim 1, wherein the first sequencing adaptor does not include a staple match sequence and the first staple is complementary in part to the first sequencing adaptor sequence.

4. The method of claim 1, further comprising amplifying the ligation products by polymerase chain reaction (PCR) using at least one primer complementary to a portion of either the first sequencing adaptor or the second sequencing adaptor.

5. The method of claim 4, further comprising removing the first staple and the second staple from the ligation products prior to amplifying the ligation products by PCR.

6. The method of claim 1, further comprising, following the adding the DNA ligase, adding a first staple-complement sequence that hybridizes to the first staple with a higher binding energy than the ligation products and a second staple-complement sequence that hybridizes to the second staple with a higher binding energy than the ligation products.

7. The method of claim 1, further comprising:
adding, to the vessel:
a third staple that is complementary in part to a second 5'-end sequence present on the second subset of DNA strands storing a portion of a second digital file and complementary in part to the first sequencing adaptor, and
a fourth staple that is complementary in part to a second 3'-end sequence present on the second subset of DNA strands storing the portion of the second digital file and complementary in part to the second sequencing adaptor.

8. The method of claim 7, further comprising:
sequencing the ligation products by a sequencing technique that uses the first sequencing adaptor and the second sequencing adaptor, wherein the ligation products have a sequence comprising the first sequencing adaptor, the second 5'-end sequence, a payload sequence of the second subset of DNA strands encoding a portion of the second digital file, the second 3'-end sequence, and the second sequencing adaptor; and
separating sequence reads of the ligation products having the payload sequence storing a portion of the first digital file from the ligation products having the payload sequence storing a portion of the second digital file based on at least one of:
the 5'-end sequence associated with the first digital file and the second 5'-end sequence associated with the second digital file, or
the 3'-end sequence associated with the first digital file and the second 3'-end sequence associated with the second digital file.

9. The method of claim 1, further comprising sequencing the ligation products by a DNA sequencing technique that uses the first sequencing adaptor and the second sequencing adaptor.

10. The method of claim 9, further comprising:
receiving DNA sequence read data from a DNA sequencer that implements the DNA sequencing technique; and
identifying reads within the DNA sequence read data that encode a portion of the first digital file based at least in part on the presence of the 5'-end sequence or the 3'-end sequence in the reads.

11. The method of claim 1, wherein the cooling is performed gradually over about one hour.

12. A method of selectively preparing a DNA strand for sequencing, the method comprising:
in a DNA pool comprising a first DNA strand with a first identification (ID) sequence and a second DNA strand with a second ID sequence:
contacting the DNA pool with a sequencing adaptor;
contacting the DNA pool with a staple complementary in part to the first ID sequence of the first DNA strand and complementary in part to a first end sequence of the sequencing adaptor, wherein the staple is not complementary the second ID sequence of the second DNA strand; and
contacting the DNA pool with DNA ligase, thereby attaching the sequencing adaptor to the first DNA strand without attaching the sequencing adaptor to the second DNA strand.

13. The method of claim 12, wherein the first ID sequence indicates that nucleotides in a payload sequence of the first DNA strand encode a portion of a digital file, wherein the DNA pool contains multiple DNA strands with the same ID sequence but different payload sequences.

14. The method of claim 12, further comprising:
contacting the first DNA strand with a primer complementary to a second end sequence of the sequencing adaptor; and
amplifying the first DNA strand by PCR using the primer.

15. The method of claim 14, further comprising removing the staple from the first DNA strand prior to amplifying the first DNA strand by PCR.

16. The method of claim 12, further comprising heating the first DNA strand to a first temperature and prior to contacting the first DNA strand with the DNA ligase, cooling the DNA strand to a second temperature lower than the first temperature.

17. The method of claim 16, wherein the cooling is performed gradually over about one hour.

18. The method of claim 12, further comprising sequencing the first DNA strand with a DNA sequencing technique that uses the sequencing adaptor.

19. The method of claim 12, further comprising, following contacting the DNA pool with DNA ligase, adding a staple-complement sequence that hybridizes to the staple with a higher binding energy than to a ligation product formed from the sequencing adaptor and the first DNA strand.

20. A method comprising:
adding, to a vessel containing DNA strands from a DNA pool:
a first staple that is complementary in part to a 5'-end sequence present on multiple DNA strands in the DNA pool and complementary in part to a first sequencing adaptor region, the first sequencing adaptor region including a first sequencing adaptor sequence and a first sequencing primer binding region,
a second staple that is complementary in part to a 3'-end sequence present on the multiple DNA strands in the DNA pool and complementary in part to a second sequencing adaptor region, the second sequencing adaptor region including a second sequencing adaptor sequence and a second sequencing primer binding region,
the first sequencing adaptor region, and
the second sequencing adaptor region;
heating the vessel to a first temperature;
cooling the vessel to a second temperature lower than the first temperature; and
adding, to the vessel, DNA ligase to create ligation products, the ligation products include a subset of the DNA strands from the DNA pool, the subset having a sequence comprising the first sequencing adaptor region, the 5'-end sequence, the 3'-end sequence, and the second sequencing adaptor region; and
after adding the DNA ligase, adding a first staple-complement sequence that hybridizes to the first staple with a higher binding energy than the ligation products and a second staple-complement sequence that hybridizes to the second staple with a higher binding energy than the ligation products.

* * * * *